United States Patent
Cummings, Jr. et al.

(10) Patent No.: US 6,345,260 B1
(45) Date of Patent: *Feb. 5, 2002

(54) SCHEDULING INTERFACE SYSTEM AND METHOD FOR MEDICAL PROFESSIONALS

(75) Inventors: Desmond D. Cummings, Jr., Orlando, FL (US); Robert H. Shelton, Irvine, CA (US)

(73) Assignee: Allcare Health Management System, Inc., Forth Worth, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/039,614

(22) Filed: Mar. 16, 1998

Related U.S. Application Data (60) Provisional application No. 60/040,612, filed on Mar. 17, 1997.

(51) Int. Cl.$^7$ ............................................. G06F 17/60
(52) U.S. Cl. ............................................. 705/8; 705/9
(58) Field of Search ..................... 705/8, 9; 345/963; 364/705.08; 40/107

(56) References Cited

U.S. PATENT DOCUMENTS

| | | | | |
|---|---|---|---|---|
| 4,817,018 A | * | 3/1989 | Cree et al. | 364/518 |
| 4,819,191 A | * | 4/1989 | Scully et al. | 364/518 |
| 5,050,077 A | * | 9/1991 | Vincent | |
| 5,124,912 A | * | 6/1992 | Hotaling et al. | 364/401 |
| 5,197,000 A | * | 3/1993 | Vincent | |
| 5,301,105 A | * | 4/1994 | Cummings, Jr. | 364/401 |
| 5,748,907 A | * | 5/1998 | Crane | 705/2 |
| 5,764,923 A | * | 6/1998 | Tallman et al. | 705/3 |
| 5,778,346 A | * | 7/1998 | Frid-Nielsen et al. | |
| 5,848,395 A | * | 12/1998 | Edgar et al. | |
| 5,867,822 A | * | 2/1999 | Sankar | |
| 5,899,979 A | * | 5/1999 | MIller et al. | |

FOREIGN PATENT DOCUMENTS

WO  WO-9421084 A1 * 9/1994

OTHER PUBLICATIONS

Yael Li–Ron and Harry McCracken, Outlook 97 (Computer Software), PC World, Feb. 1997, vol. 15, Issue 2, p. 112.*
Karen Bodner, The Ultimate Guie to Meeting Software, Successful Meetings, Nov. 1995, vol. 44, Issue 12, p. 51.*

(List continued on next page.)

*Primary Examiner*—Sam Rimell
*Assistant Examiner*—Jennifer I. Harle
(74) *Attorney, Agent, or Firm*—John L. Sigalos; Andrew M. Hassell (57) ABSTRACT

The present invention provides a system and method for scheduling appointments at any time with a professional, such as a doctor, dentist, veterinarian, or the like, or a professional service, such as a medical testing facility and the like, even when the office of the professional or professional service is closed. The system and method relate to an asynchronous Internet, intranet, and extranet-compatible 24-hour appointment scheduling interface for making such appointments. As such, they support open-standards architecture, provide an interface for proprietary system architecture, permit off-line review and posting, permit access controls and virus protection, allow central scheduling without loss of distributed control, support encrypted messaging to ensure privacy, and include context-sensitive help. The system and method also embrace and integrate over the Internet all of the existing office administration scheduling packages for professional offices, such as doctors' offices, regardless of the platforms used, i.e., PC, Apple or UNIX platforms, thereby permitting users to schedule and confirm, for example, doctor appointments in one consistent interface, regardless of the hardware or software utilized by either the party seeking to schedule an appointment or the individual doctor involved.

43 Claims, 3 Drawing Sheets

OTHER PUBLICATIONS

Tom Marshall, Organizer's Brains Now Match Its Pretty Face—Version 2.0 is Much Improved, But Lots' Crummy Documentation and Support Don't Do It Justice, Infoworld, Mar. 20, 1995, pp. 87 and 90.*

Tariq K. Muhammad, How Suite It Is, Black Enterprise, Apr. 1997, vol. 27, Issue 9, p. 40.*

Sun Ying Tam, Nuts + Bolts, Home PC, Dec. 1997, vol. 4, Issue 12, p. 185.*

Lori Grunin, Working at Home, Home PC, Jul. 1997, vol. 4, Issue 7, p. 4.*

Daniel Bobrow, Sidestepping Caller ID, Dental Economics, Oct. 1997pp. 58–60.*

Merriam–Webster's Collegiate Dictionary, www.m–w.com (Definitions of appointment and engagement).*

"U.S. Wide Area Wireless Data Networks: Overview" Datapro Information Services, pp. 1–19, Apr. 1996.*

* cited by examiner

SCHEDULING INTERFACE SYSTEM AND METHOD FOR MEDICAL PROFESSIONALS

CROSS REFERENCE TO RELATED APPLICATION

This application claims the benefit of prior filed co-pending U.S. Provisional Patent Application No. 60/040,612, filed Mar. 17, 1997.

BACKGROUND OF THE INVENTION

The present invention relates to a system and method for scheduling appointments that is compatible for Internet, intranet, and extranet use. It relates to an asynchronous Internet and intranet-compatible scheduling interface for booking appointments with a professional, such as a doctor, or a professional service, such as a medical testing service (X-rays, blood tests, and the like), even when scheduling details may contain sensitive or highly personal information and when the office of the professional or professional service is closed.

At the present time it is not possible to schedule appointments with a doctor, for example, when the doctor's administrative offices are closed. Even when the offices are open, it is occasionally difficult to access the administrative office in order to schedule an appointment because of the number of telephone calls that such professionals often receive and the small staff-to-doctor levels used in some practices. At the present time there are also services which, on behalf of such patients, attempt to contact doctors' offices during the hours when their administrative offices are open and available to schedule appointments. However, even these services have difficulty in that if the doctor's line is busy or support personnel temporarily on break, they cannot get through to the administrative offices to set an appointment at the time desired and thereby complete the service to their client. It is also not possible for them to schedule appointments when a doctor office is closed.

Medical professionals such as doctors often employ answering services during the hours when their administrative offices are closed, but such services are not in a position to schedule appointments and simply will take messages and pass them on. In some instances such messages are conveyed to the office administrator on the next business day, or in the case of a perceived medical emergency, such messages may be sent to the doctor in the form of a wireless page for him to act on, if he can be reached.

Both circumstances are known to result in increased patient anxiety, in increased risk of aggravating an existing medical condition requiring immediate medical attention and for increasing the loss of care when such callers use more costly services such as hospital emergency rooms when they cannot contact their doctor or adequately satisfy their need for medical advice.

In none of these systems, however, has it been possible for the patient to have access to the doctors' appointment schedule for the following day or days to enable a patient or other party to schedule an appointment with the doctor at an appointed time. Nor is it possible at the present time to permit such access to schedule an appointment while at the same time protecting the privacy of the person attempting to schedule the appointment, as well as information regarding the doctors' other appointments.

SUMMARY OF THE INVENTION

The present invention overcomes the problems of the prior art and is directed to a system and method for permitting scheduling of appointments for professionals and professional services when their administrative offices are closed.

Briefly stated, the present invention provides a system and method for scheduling appointments at any time with a professional, such as a doctor, dentist, veterinarian, or the like, or a professional service, such as a medical testing facility and the like, even when the office of the professional or professional service is closed.

As more particularly set forth below, the system and method relate to an asynchronous Internet, intranet, and extranet-compatible 24-hour appointment scheduling interface for making such appointments. As such, they support open-standards architecture, provide an interface for proprietary system architecture, permit off-line review and posting, permit access controls and virus protection, allow central scheduling without loss of distributed control, support encrypted messaging to ensure privacy, and include context-sensitive help.

The system and method also embrace and integrate over the Internet all of the existing office administration scheduling packages for professional offices, such as doctors' offices, regardless of the platforms used, i.e., PC, Apple or UNIX platforms, thereby permitting users to schedule and confirm, for example, doctor appointments in one consistent interface, regardless of the hardware or software utilized by either the party seeking to schedule an appointment or the individual doctor involved.

OBJECTS AND FEATURES OF THE INVENTION

It is a general object of the present invention to provide a fully integrated system and method for an asynchronous Internet, intranet- and extranet-compatible scheduling interface for scheduling appointments.

It is an object of the present invention to provide a system and method for receiving notification of an available appointment time and for scheduling appointments even when the administrative offices are closed.

It is another object of the present invention to allow for central scheduling without loss of local control.

It is yet another object of the present invention to permit users to schedule and confirm doctors' appointments in one consistent interface regardless of the computer hardware or software selected by their individual physician and regardless of whether the physicians' office does or does not utilize a computer.

It is also an object of the present invention to permit users to schedule and confirm doctors' appointments or medical facility appointments, regardless of the computer hardware or software they employ and even if they do not utilize a computer at all.

It is a further object of the present invention to resolve what has been an historical impediment to the smooth operation of after-hours call centers and doctor answering services, namely to complete the patient service by reviewing all available appointment times for all doctors in a field of specialization and geographic area proximate to the patient, and having selected the best one or several suited, scheduling an appointment when the medical professional's offices are closed.

It is still another object of the present invention to automate the scheduling process on an enterprise-wide basis and incorporating highly fragmented medical offices and individually-owned physician practices.

It is a feature of the present invention to replace a medical professional's answering service and traditional beeper and thereby enabling accurate diagnoses of patient conditions and then scheduling the appropriate medical service.

It is another object of the present invention to promote the interoperability of widely-used desktop applications, databases and operating system environments within the deeply fragmented healthcare industry.

It is yet another feature of the present invention to embrace and integrate over the Internet the leading present and future office administration and scheduling packages, contract management programs, personal information manager programs, personal data assistant (PDA) hardware, wireless two-way beepers and wireless beepers running on existing, as well as future desktop and client/server environments.

It is still another feature of the present invention to interface with proprietary electronic data systems for healthcare.

It is a further feature of the present invention to concurrently provide a foundation for easy migration of scheduling applications in the future.

It is a feature of the present invention to permit patients to schedule and confirm doctors appointments within the system interface without having to be concerned that their Web browser may not be directly compatible with the computer hardware or software selected by their physician and, if preferred, without either party being required to utilize a computer.

It is another feature of the present invention to eliminate any concern with hardware or software compatibility, and thereby to provide a seamless user, developer, and administrator capability.

It is yet another feature of the present invention to reduce unnecessary hospital emergency room visits, avoid the aggravations of waiting rooms, increase patient satisfaction, reduce malpractice cases and lower health plan costs by enabling patients to receive timely and accurate information and assistance, as well as to check for availability of and schedule appointments at hours when their physician's office is closed.

It is still another feature of the present invention to reduce the number of after-hours emergency calls (which do not involve emergency medical assistance) which physicians must handle by shifting these to scheduled appointments during normal office hours.

It is a further feature of the present invention to significantly reduce capital cost and administrative expenses by eliminating any requirement that each physician invest in identical computer hardware, software or dedicated interconnect lines.

It is a feature of the present invention to significantly reduce capital cost and administrative expenses by eliminating any requirement for installing a local-area network (LAN) or wide-area network (WAN) in order to achieve the benefits of the instant invention.

It is yet another feature of the present invention to reduce training and on-going support requirements involved in systems that require proprietary hardware, software, LAN or WAN.

It is still another feature of the present invention to curtail the number of instances when calls are made to request an appointment for an already booked time, or for a time when the doctor is intending to be out of his or her office.

It is a further feature of the present invention to support physicians' offices that employ a manual calendar method rather than an electronic scheduler or other computer-based systems and methods.

It is another feature of the present invention to enhance the security of the physician's computer and thereby virtually eliminate the possibility of unknown callers successfully obtaining access to patient records or other data maintained by the physician.

It is yet another feature of the present invention to permit call centers to replace traditional answering services.

It is still another feature of the present invention to reduce overhead for some physicians in the area of medical malpractice insurance premiums in consideration of the significantly improved patient records, consistency and high standards of patient care made possible through employing the instant invention.

It is a further feature of the present invention to enable migration of new computer-based patient record systems and applications as set forth in U.S. Pat. No. 5,301,105.

It is a feature of the present invention to provide for easy migration of new computerbased patient record systems and applications in the future as set forth in co-pending U.S. patent application Ser. No. 09/025,279, filed Feb. 17, 1997 by one of the co-inventors hereof.

It is still another feature of the present invention to permit a caller to quickly check the availability of numerous physicians in order to determine the one who's availability and geographical location are best suited to the time when an appointment is desired.

It is also a feature of the present invention to incorporate herein the payment verification functions set forth in U.S. Pat. No. 5,301,105.

It is a further feature of the present invention to lay the foundation for incorporating the adjudication and utilization review functions set forth in U.S. Pat. No. 5,301,105.

It is another feature of the present invention to permit numerous organizations and software developers to work in parallel to write enhancements, to customize individual installations and to provide additional functionality for scheduling.

It is still another feature of the present invention to permit each doctor's office to function autonomously and yet simultaneously to obtain many of the benefits and efficiencies of large, fully-integrated health practices and managed care organizations.

It is still another feature of the present invention to protect the privacy of both the patient desiring to schedule an appointment, as well as any and all patients already included on the physician's schedule under consideration and review.

It is a feature of the present invention to leave the control over a physician's calendar in the individual doctor's office with his or her own administrative personnel.

It is another feature of the present invention to permit its operation asynchronously over the Internet.

It is yet another feature of the present invention to permit appointments to be scheduled both through a call center as well as directly over the Internet.

It is also a feature of the present invention to permit appointments to be confirmed through a coordination center, directly over the Internet, via a wireless two-way beeper or PDA, or over the telephone.

It is still another feature of the present invention to permit use with a wide number of current technologies, including Netscape Navigator and Internet Explorer browser applications, as well as numerous third-party workgroup scheduling and calendar programs, contract management programs, PIM applications and PDA programs, written with Netscape open-standards and/or Microsoft ActiveX (OLE) interfaces running on PC, Apple Macintosh and UNIX platforms.

It is a further feature of the present invention to enable inclusion therein of numerous physicians who have not yet upgraded their administrative office computers to newer operating programs, such as Windows, and who still operate using older 386- and 486-based processors.

It is a feature of the present invention to support a DOS-based scheduler solution in order to support older computer systems with very limited memory resources and slower modem speeds.

It is also a feature of the instant invention to permit telephone and wireless communication-based scheduling in order to permit use of the invention by physicians away from their offices and those who do not have any computer hardware or software.

It is yet another feature of the present invention to provide access from all other proprietary legacy development environments, databases and software applications that include scheduling capabilities.

It is still another feature of the present invention to assure smooth inter-operability with future software and physicians' office productivity templates.

It is a feature of the present invention to allow the individual office administrator to make his or her own decision concerning which computer system, if any, and which scheduling software, if any, they prefer to use.

It is another feature of the present invention to display the same graphical user-interface (GUI) to all callers notwithstanding which hardware or software systems are used in the physician's office for scheduling.

It is also a feature of the present invention to permit communication of the physicians' appointment schedules and availability to persons using a telephone in lieu of a computer.

It is yet another feature of the present invention to update the current appointment calendar with the times of any tentative bookings that have been made by other authorized callers after a physician's administrative offices close.

It is still another feature of the present invention to automatically reserve sufficient time based upon the individual physician's or medical facility's procedure requirements.

It is a further feature of the present invention to provide for a tentative booking to be rescheduled after the physician's office opens.

It is a feature of the present invention to collect any pre-screening and pre-certification information in order to expedite the administrative requirements at the time of the patient's appointment.

It is another feature of the present invention to remind the patient of any special instructions required for the appointment, such as food prohibitions before tests, records to bring and directions to the physician's office.

It is yet another feature of the present invention to enhance network security by limiting access to the physician's computer only to connections made from an authenticated scheduling server.

It is still another feature of the present invention to optimize use of the Internet and World Wide Web as a distribution channel without compromising the vital health-care and professional service industry considerations of confidentiality, privacy and economics.

It is a further feature of the present invention to provide complete security and an off-site audit trail.

It is a feature of the present invention to allow the physician's office to keep his or her computer physically disconnected from the Internet, intranet or extranet, except during the batch process of communicating with an authenticated server.

DETAILED DESCRIPTION

While the instant invention is applicable broadly to systems and methods for scheduling appointments with professionals, such as doctors and professional services, such as X-ray screening, blood testing, and the like, facilities, it will be described with respect to scheduling doctor appointments.

Figure 1:
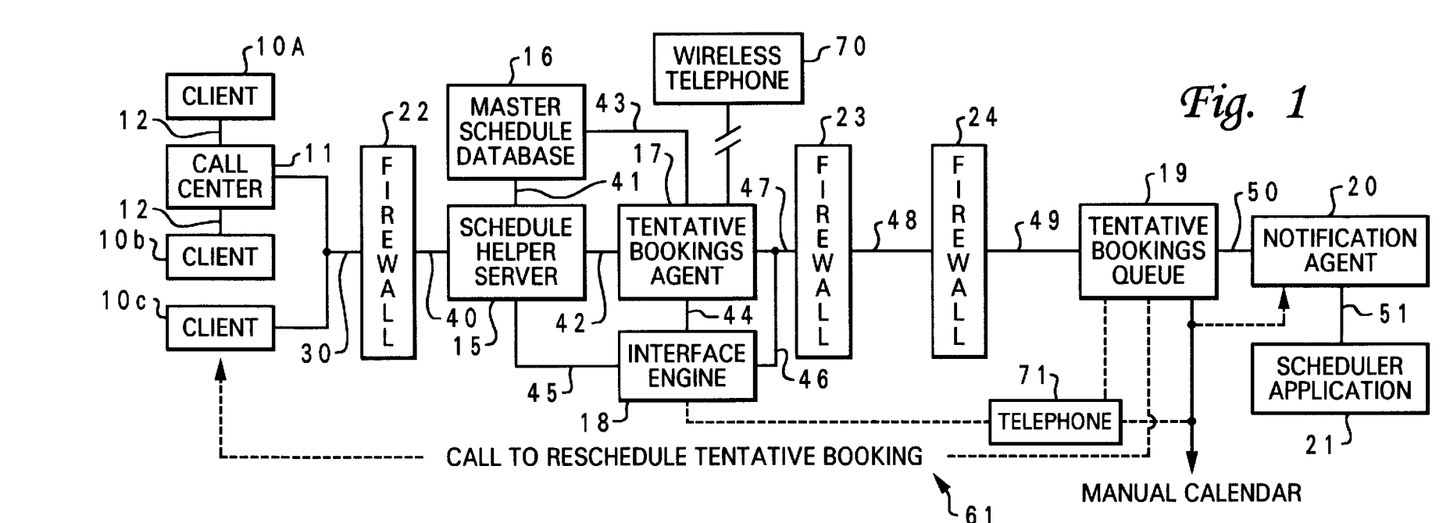
FIG. 1 is a block diagram depicting principal functions of the instant invention as applied to scheduling a medical appointment with a doctor.

Referring to the drawings, FIG. 1 depicts the principal system components and method steps of a preferred system in accordance with the principals of the invention. Shown as 10a, 10b and 10c are clients, i.e., patients requiring a doctor appointment or trying to schedule some procedure at a medical facility. Shown as 11 is a coordination center, such as and preferably an attended or unattended call center, to which clients can call through conventional telephone lines 12, rather than trying to contact the doctor to schedule such appointment themselves. The call center 11 is any conventional stand-alone organization which accepts calls from individuals seeking medical advice, pre-certification for Emergency Room care and/or that arranges appointments with doctors. They can act, in fact, as a referral-type service. An example thereof is Access Health's Ask-a-Nurse® service licensed to many hospitals. Calls received at such center by telephone are answered by a registered nurse with an average of 10 to 15 years emergency room experience who assists the caller to assess the seriousness of injuries or symptoms, and determines appropriate options for medical evaluation. Many of the inquiries, it has been found, do not require emergency room treatment, or a doctor visit. If no emergency room treatment is required, but a doctor visit is concluded to be the appropriate treatment option, the caller can be referred to an appropriate physician (appropriateness being based on geographical location, field of specialization, type of payment means accepted, caller preference, and the like). In effect, this is a sophisticated triage procedure whereby, if necessary, the patient can be sent to the Emergency Room where their waiting time and need to complete forms will be greatly reduced or eliminated and, if not necessary, a physician's office, or minor self-help treatment advised. Presently, such call center system can try to schedule a doctor appointment, but must keep the caller on the line, must call the doctor's office to check for available appointment times and try to set up an appointment and, obviously, if the doctor's office is closed or the available times not suitable cannot schedule any appointment. In FIG. 1, clients 10a and 10b are shown as contacting such call center 11; and client 10c is shown seeking directly to make his own appointment.

Before describing the system and method in greater detail and referring to the drawings, it will be evident that the client 10c and call center 11 will need to have an adequate conventional computer terminal and printer and that the terminal be connected as by telephone 13 or 14, or satellite or other means to the Web by means of any conventional Internet service provider. It is also evident that this interface can be a telephone connection to an interactive system producing audio feedback based on telephone key pad prompts by the user. Links 30 and 40 to 51 inclusive are likewise conventional communication paths such as telephone lines, internal connectivity, or the like, all operating through the Internet through Internet firewall gateways 22, 23, and 24. All of these are conventional presently existing techniques for accessing and gathering information from the Internet. It is also possible, of course, to utilize an intranet, extranet, LAN or WAN, in lieu of, or in concert with the Internet.

By operating through a conventional Internet service provider, there will also be available to the client an electronic mail function linked to the processing system, i.e., the computer and printer of client 10c and call center 11.

In short, the instant system and method utilize existing computer hardware and existing communication links, such as the Internet and phone system, in order to access data bases without compromising the vital considerations of privacy of patient information and rigorous control of access, as well as retaining records of the access requester.

Moreover, as used herein, the terms, "server", "interface engine", "queue", and "agent" have the standard meanings used by those skilled in this art and is intended to include those devices in the future which supplant the same; e.g. any chip-based, multiple input/output manager used in place of present "servers." The term "Master Schedule Data Base" means a data base having such information as the appointment times already booked, blocked, and available for the various doctors in the system, as well as instructions and/or rules pertaining to an appointment or type of other conventional appointment, and other related information. Such data base can be contained on a digital computer or like device. "Tentative Bookings Agent" means the data base holding the client's schedule for review by the doctor's office staff when such office next is open or that can, optionally, be transmitted via wireless pager to the doctor. Lastly, "Firewall" refers to the usual known security layer(s) provided in computerized systems to permit access to certain files only to those having the necessary "password(s)", "digital certificates" and the like, and to protect against viruses and unauthorized tampering. The Internet, for example, gives users their own private password.

Figure 2:
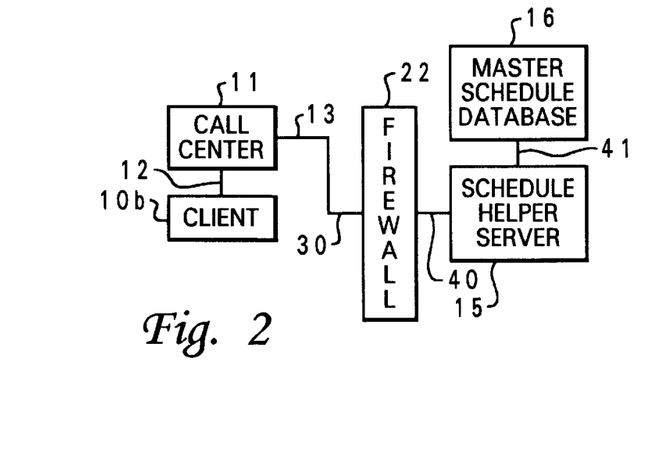
FIG. 2 is a block diagram illustrating process flow of a portion of the invention relating to the search of availability of doctor appointment times and dates.

FIG. 2 illustrates how client 10b can schedule an appointment when a doctor's office is closed utilizing call center 11 in order to check when a physician is available to see a patient. While client 10b is on the line, call center 11 can log onto the Web from any Web browser. With proper security clearance and verification, server 15 permits access to online master schedule database 16, which contains and displays the appointment times and dates for all physicians on the system, i.e., showing those times when these physicians are willing to accept tentative appointment bookings Such database 16 can be periodically or continuously updated, depending upon the nature and the type of connection to each physician's office.

Database 16 will indicate when the records were last updated for this physician, any tentative bookings that have been made since that time, and the normal office hours. In addition, database 16 can contain specific requirements as to duration of appointments, the physician's instructions, and standing orders (such as whether the physician should be paged while the patient is still on the line) and, if connected to a fully integrated system as in U.S. Pat. No. 5,301,105, connection to verify payor status, and other pertinent information.

Figure 3:
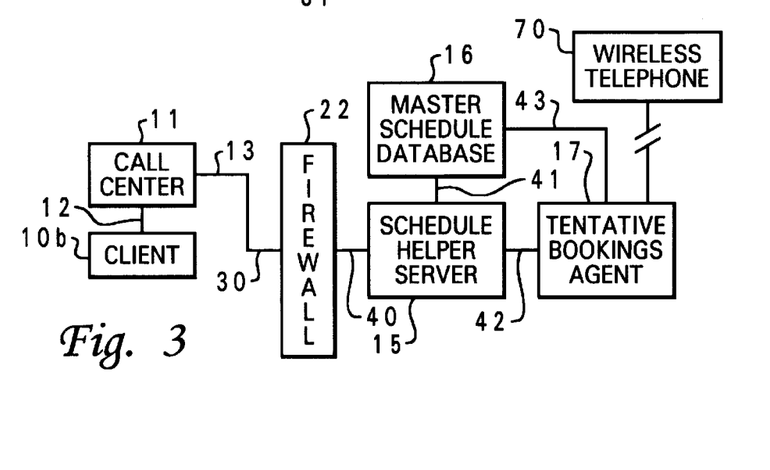
FIG. 3 is a block diagram illustrating process flow of a portion of the invention relating to scheduling a tentative appointment time and date.

FIG. 3 illustrates how a tentative appointment is scheduled, i.e., "booked". The doctors' available appointment, as noted, are displayed. Conventional clicking on the icon associated with any open block of time shown on a particular physician's schedule in database 16 will bring up a dialogue box where the patient's name can be typed, together with a brief summary of the nature of the medical concern, a contact number where the patient can be reached if the appointment must subsequently be rescheduled and any other pertinent facts. Such dialogue box is, in effect, a tentative booking form and may thus request additional pertinent information. For example, when the client is not an existing patient of the doctor, preregistration and billing information can also be requested prior to accepting the tentative booking. Additional fields of information can be provided to detail the medical concern and if the call was initiated from the call center, these fields can be automatically completed from the results of the telephone triage.

The tentative booking form can be programmed with default rules in accordance with instructions provided by the physician concerning the duration of appointment and other instructions. Once the form has been completely filled out, clicking the appropriate key will automatically update master schedule database 16 and hold the tentative booking for delivery to the physician's office in tentative booking agent 17. If specified by the pre-programmed instructions of the physician, tentative booking agent 17 can immediately initiate a page to wireless pager 70 carried by the doctor to indicate that booking activity has occurred. If pager 70 is two-way in nature, the doctor can respond to indicate acceptance or refusal of the appointment or indicate some other action. A tentative booking confirmation screen can remind the patient of any special instructions such as food prohibitions before tests, records to bring and directions to the office. This screen will also set a time (presumably on the next business day) by which the physician's staff will call the patient if, for some reason, the appointment time must be changed.

Figures 4, 5:
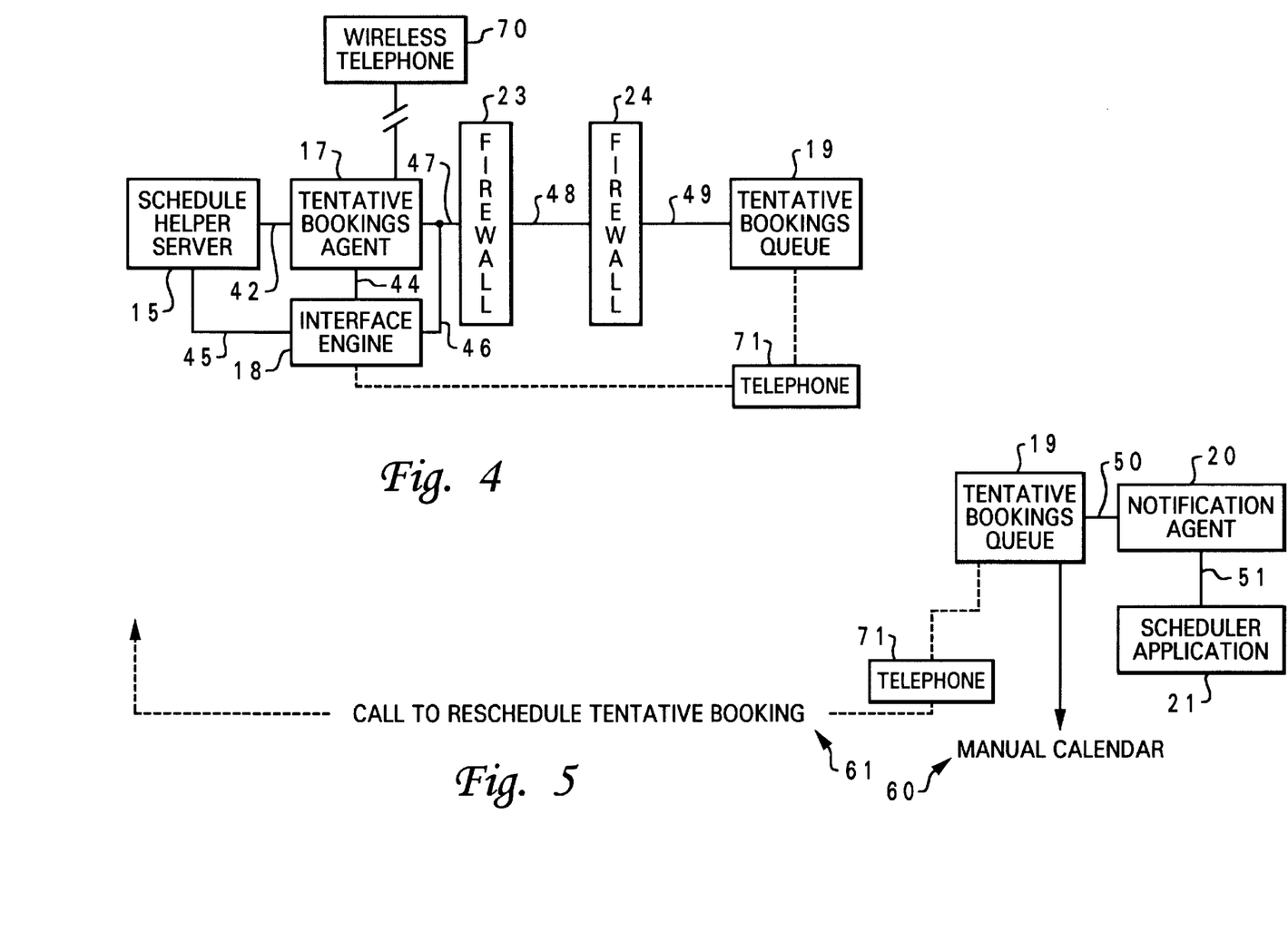
FIG. 4 is a block diagram illustrating process flow of a portion of the invention relating to retrieval and authentication by the doctor of the tentative appointment.
FIG. 5 is a block diagram illustrating process flow of a portion of the invention relating to confirmation or rescheduling of the appointment.

FIG. 4 illustrates how a tentative booking is communicated to the system in the physician's office. When the physician's office opens on the next business day, one of the morning procedures for his or her administrative staff will be to log onto the Internet and after authenticating their identity, retrieve any tentative appointments held by tentative bookings agent 17. To the extent the physician is connected in an intranet or proprietary network, this process can be done automatically by an appropriate conventional software program.

The next stage of the instant system and method will differ slightly, depending on whether the physician's office uses a manual or an electronic calendar system; and in the event they are using a computerized system, then specifically which scheduling application is being used. In all instances, tentative bookings agent 17 acts as a message-passing server, responding to the bookings requests it is holding and the record of which computer platform, Web browser and calendar system each physician's office employs.

Where required, interface engine 18 automatically translates these bookings into the appropriate protocols for the system employed by the caller and then transfers the tentative booking information over the network to tentative bookings queue 19 on the physician's office machine, together with any attached reports that are held for the physician's review and the patient's permanent file. This action will automatically place an indication on master schedule database 16 that the physician's office is open and notify inquirers that all appointments should now be scheduled directly with the doctor's office staff.

Since it is well known that physicians have been one of the last groups to widely use computers in their administrative offices, FIG. 4 also indicates that those offices which still use fully manual scheduled systems can indicate a call using a traditional telephone 71. In those instances, the physician's office staff will place a call to a special number that connects to interface engine 18. Using the telephone key pad, the caller may then verify his identity, key-in a request to update his or her calendar with tentative bookings (if any) held in Tentative bookings Agent 17 and indicate by depressing specified keys if such bookings are accepted or rejected; provided, however, that in the latter case, the doctor's staff will be requested to telephone the caller.

FIG. 5 illustrates the activity within the doctor's office following completion of the tentative booking. After the call is concluded, the workflow will differ, as noted above, depending on whether the physician's office uses a manual or an electronic calendar. When a manual calendar or conventional telephone 71 is used, the office staff will simply transcribe any new appointments into the corresponding open space on the manual calendar 60 or, alternatively, call the patient 61 if the actual appointment date or time must be changed from the time recorded in tentative booking queue 19.

When a computerized scheduler application 21 is used, the process of updating the office calendar can be partially or fully automated. Depending on the specific brand of scheduling or practice management application employed in the physician's office, clicking on the appropriate button next to each new booking will automatically cause notification agent 20 to enter the appointment onto the physician's calendar. For other brands of scheduler or practice management application, this result will be accomplished by drag and drop functionality; and for still others, by either typing or copying, then posting, the data into the calendar at the appropriate day and time. Confirmation or re-scheduling can be offered by a telephone call or, if the patient has e-mail, by such means.

Figure 6:
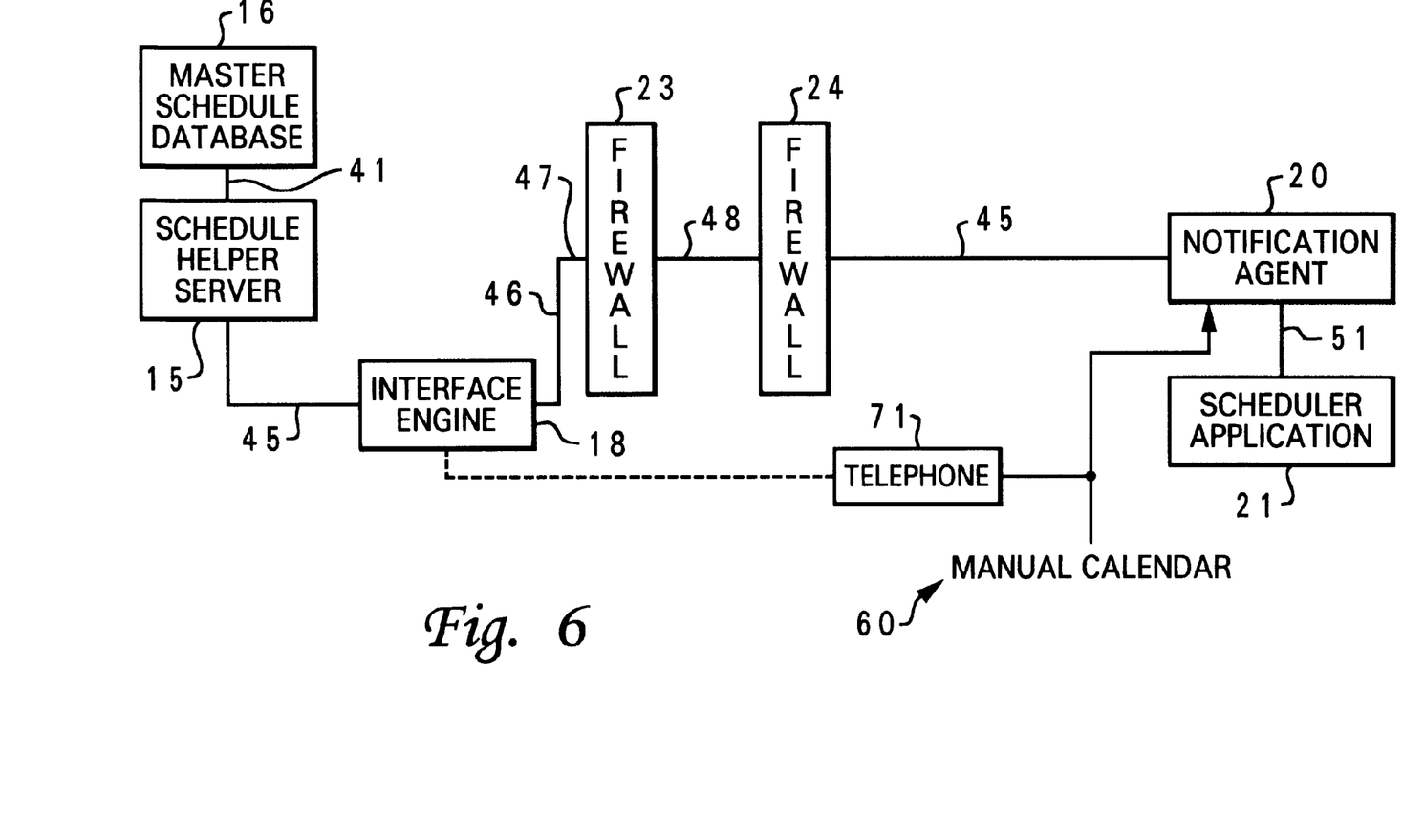
FIG. 6 is a block design illustrating process flow of a portion of the invention relating to updating the availability of doctor appointment time and dates.

As illustrated by FIG. 6, updates to the master schedule database 16 are simply performed by reversing the workflow at the conclusion of each business day, or periodically during the day in the interface of an intranet, LAN, or WAN, where continuous updates are possible. When an electronic calendar is employed, logging into the Web site will prompt notification agent 20 to transmit any changes that have occurred in the physician's schedule since the last update.

Where a manual system is employed, a graphical user interface (GUI) will prompt the office staff to enter the times when any new appointments were booked or changes made. Since master schedule database 16 will only record availability, this update will merely require a few keystrokes such as indicating an "X" for "booked", "B" for "blocked", "H" for "at hospital", etc. To the extent the physician's office does not utilize a computer, this same information can be updated by calling a designated number by telephone and, for example, entering the date and time and pressing the star key for "booked", the pound key for "blocked", etc.

The instant system and method assure that all parties' interests are protected at all times. The invention will dramatically reduce response times and significantly improve service while still maintaining total schedule control at the local physician's office. The use of open-standards allows for more rapid integration of numerous third-party scheduling applications, as well as for the creation of custom in-house solutions and at the same time permits the ready integration of proprietary systems and networks such as the IMS MEDACOM system, America's largest health information network connecting over 50,000 physicians.

Encryption of all communications, as by using SSL 3.0, and more robust Internet security standards that will supersede it in the future, will prevent tampering, eavesdropping and message forgery. By the same token, computer networks are only as strong as their weakest link, which often occurs at the gateway. Positioning the instant system at this gateway to the physicians' computer system enhances this network security, because the only connections made are with the authenticated server 15. This virtually eliminates the possibility of unknown callers successfully tapping into the physician's computer.

The ubiquity and ease of use of the instant invention will also permit call centers, such as call center 11, to expand their services to physicians who adopt the invention by offering the generic resource of their call centers as an alternative to the doctor's normal answering service. In order to do this, the physician's staff will merely forward the main phone number to call center 11 for attention when his or her office is closed. Currently these after-hours callers are being handled by a receptionist or an answering service who is often not well trained, does not have prior medical experience and whose sole options are to take a message or issue a page to the doctor on call. Once this service is replaced by call center 11, incoming callers will be handled by a professional staff of seasoned nurses who will be able to use the conventional triage protocols and scheduling systems available through call center 11 to better serve the patient in the doctor's absence. Such service can be offered for about the same monthly cost as the doctors' current answering and beeper service, and will greatly enhance the patients' sense of timely and competent service, decrease the number of after-hours calls and beeper interruptions on non-emergency medical matters experienced by physicians, and potentially lead to reductions in malpractice suits and cost of malpractice insurance, and thus lower overall cost to patients.

While the invention has been described in connection with a preferred embodiment, it is not intended to limit the scope of the invention to the particular form set forth but, on the contrary, it is intended to cover such alternatives, modifications, and equivalents as may be included within the spirit and scope of the inventions as defined by the appended claims.

What is claimed is:

1. An asynchronous system for scheduling appointments for a plurality of patients at medical facilities of a plurality of medical professionals comprising:

(a) a master schedule electronic data base having:
   a. a data base of existing appointments for said medical professionals,
   b. means for updating said data base;
   c. another data base of available appointment times for said medical professionals,
   d. means for updating said another data base,
   e. tentative appointment data base storage means for electronically storing records of tentative appointments for said patients with said medical professionals, means for asynchronously requiring subsequent electronic confirmation or rejection of said tentative appointments, and
   f. means for electronically communicating indicia of said tentative appointments to said medical professionals;
(b) a coordination center having:
   a. communication means including a telephonic link,
   b. means including said telephonic link for individually effecting telephonic communication with said patients;
   c. means for making said tentative appointments for said patients with said medical professionals and for communicating indicia of said tentative appointments to said master schedule data base;
(c) means including said tentative appointment storage means responsive to receipt of said indicia of said tentative appointments for storing said indicia; and
(d) means responsive to inquiry by an inquiring one of said medical professionals of tentative appointments made for said inquiring one of said medical professionals to electronically transmit to said inquiring one of said medical professionals indicia of tentative appointments made for said inquiring one of said medical professionals.

2. A system according to claim 1 wherein said master schedule data base is contained in a digital computer.

3. A system according to claim 1 further including means for periodically updating said master schedule data base.

4. A system according to claim 1 further including means for continuously updating said master schedule data base.

5. A system according to claim 1 wherein said master schedule data base further includes means indicating the most recent date of updating said master schedule data base.

6. A system according to claim 5 wherein said master schedule data base further includes indicia indicative of any tentative bookings made since said most recent date of updating said master schedule data base.

7. A system according to claim 1 wherein said another data base includes indicia indicating normal office hours of said medical professionals.

8. A system according to claim 1 wherein said system further includes form means establishing a uniform form for accepting entry of patient data.

9. A system according to claim 1 wherein said system further includes form means for accepting entry of patient data for a plurality of said medical professionals, and wherein said system includes means for customizing said form according to specifications established by said medical professionals.

10. A system according to claim 1 further including wireless pagers at said medical professionals and means for transmitting to said wireless pagers said indicia of said tentative appointments.

11. A system according to claim 1 further including a tentative booking queue data base located at one of said medical professionals for storing tentative booking entries made for said one of said entities.

12. A system according to claim 1 wherein said coordination center is attended.

13. A system according to claim 1 wherein said coordination center includes an attended call center and central scheduling server.

14. The system according to claim 1 wherein said coordination center includes a central scheduling server.

15. An asynchronous system for scheduling appointments for a plurality of patients at medical facilities of a plurality of medical professionals comprising:
(a) a master schedule electronic data base having:
   a. a data base of existing appointments for said medical professionals, and
   b. means for updating said data base;
(b) another electronic data base having:
   a. available appointment times for said medical professionals, and
   b. means for updating said another data base;
(c) a tentative booking electronic data base having:
   a. tentative appointment storage means for electronically storing records of tentative appointments for said patients with said medical professionals, means for asynchronously requiring subsequent confirmation or rejection of said tentative appointments, and
   b. means for electronically communicating indicia of said tentative appointments to said medical professionals;
(d) a coordination center having:
   a. communication means including a telephonic link,
   b. means including said telephonic link for individually effecting telephonic communication with said patients;
   c. tentative booking means for making tentative appointments for said patients with said medical professionals and for communicating indicia of said tentative appointments to said tentative booking data base;
(e) means including said tentative booking means responsive to receipt of said indicia of said tentative appointments for storing said indicia; and
(f) means responsive to inquiry by an inquiring one of said medical professionals of tentative appointments made for said inquiring one of said medical professionals to electronically transmit to said inquiring one of said medical professionals indicia of tentative appointments made for said inquiring one of said medical professionals.

16. A system according to claim 15 wherein said master schedule data base is contained in a digital computer.

17. A system according to claim 15 further including means for periodically updating said master schedule data base.

18. A system according to claim 15 further including means for continuously updating said master schedule data base.

19. A system according to claim 15 wherein said master schedule data base further includes means indicating the most recent date of updating said master schedule data base.

20. A system according to claim 19 wherein said master schedule data base further includes indicia indicative of any tentative bookings made since said most recent date of updating said master schedule data base.

21. A system according to claim 19 wherein said another data base includes indicia indicating normal office hours of said medical professionals.

22. A system according to claim 15 wherein said system further includes form means establishing a uniform form for accepting entry of patient data.

23. A system according to claim 15 wherein said system further includes form means for accepting entry of patient data for a plurality of said medical professionals, and wherein said system includes for customizing said form according to specifications established by said medical professionals.

24. A system according to claim 15 further including wireless pagers at said medical professionals and means for transmitting to said wireless pagers said indicia of said tentative appointments.

25. A system according to claim 15 further including a tentative booking queue data base located at one of said medical professionals for storing tentative booking entries made for said one of said medical professionals.

26. A system according to claim 15 wherein said call center is attended.

27. A system according to claim 15 wherein said coordination center includes an attended call center and central scheduling server.

28. The system according to claim 15 wherein said coordination center includes a central scheduling server.

29. A method of asynchronously supervising and controlling appointment scheduling for a plurality of patients at medical facilities of a plurality of medical professionals comprising steps of:
   (1) establishing a master centralized electronic data base to serve a plurality of medical professionals;
   (2) providing at least one call center for electronically communicating with said master data base;
   (3) electronically storing in said master data base indicia indicative of appointments available with said medical professionals at medical facilities of said medical professionals;
   (4) receiving at said call center indicia from a patient indicating a request for an appointment time with one of said medical professionals;
   (5) interrogating said master data base to determine said available appointments, and:
      (a) when said requested appointment time is available,
         (i) tentatively making said requested appointment, said appointment being tentative and requiring subsequent confirmation or rejection,
         (ii) communicating a tentative unconfirmed booking for said requested appointment time to said patient requesting said appointment, and
         (iii) communicating said tentative booking for said requested appointment time to the medical professional for whom said tentative booking is made,
      (b) when said requested appointment time is not available,
         (i) informing said patient of non-availability of said requested appointment time,
         (ii) informing said patient of available appointment times,
         (iii) requesting said patient to select from said available appointment times,
         (iv) receiving from said patient an alternative request for appointment,
         (v) communicating a tentative unconfirmed alternative booking for said alternative appointment time to said patient requesting said alternative appointment, and
         (vi) communicating said tentative alternative booking for said requested appointment time to the medical professional for whom said tentative alternative booking is made.

30. The method of claim 29 wherein the step of storing in said master centralized data base indicia indicative of appointments available at said medical professionals further includes a step of storing said indicia in a digital computer.

31. The method of claim 29 further including a step of periodically updating said master centralized data base.

32. The method of claim 29 further including a step of continuously updating said master centralized data base.

33. The method of claim 29 further including a step of including in said master centralized data base indicia identifying the most recent date of updating said master centralized data base.

34. The method of claim 33 further including a step of including within said master centralized data base indicia indicative of any tentative bookings made since said most recent date of updating said master centralized data base.

35. The method of claim 29 further including a step of including within said master centralized data base indicia indicating normal office hours of said medical professionals.

36. The method of claim 29 further including a step of preparing a standard format for accepting and entering patient data into said master centralized data base.

37. The method of claim 36 further including steps of accepting and entering patient data in said standard format and customizing said standard format according to specifications established by said medical professionals.

38. The method of claim 29 further including a step of transmitting to said medical professionals by wireless pagers data indicative of said tentative appointments.

39. The method of claim 29 further including steps of providing a tentative booking queue data base at one of said medical professionals and storing in said tentative booking queue data base tentative booking entries made for said one of said medical professionals.

40. The method of claim 29 further including a step of establishing an attended call center and central scheduling server.

41. The asynchronous system for scheduling appointments for a plurality of patients at medical facilities of a plurality of medical professionals according to claim 1 wherein said coordination center is attended and includes a medicallytrained person responsive to information imparted thereto by said patients for pre-screening said patients.

42. The asynchronous system for scheduling appointments for a plurality of patients at medical facilities of a plurality of medical professionals according to claim 15 wherein said coordination center is attended and includes a medically-trained person responsive to information imparted thereto by said patients for pre-screening said patients.

43. The method of asynchronously supervising and controlling appointment scheduling for a plurality of patients at medical facilities of a plurality of medical professionals according to claim 29 further including steps of including at said call center a medically trained person, and pre-screening said patients.

* * * * *

UNITED STATES PATENT AND TRADEMARK OFFICE
CERTIFICATE OF CORRECTION

PATENT NO.   : 6,345,260 B1
DATED        : February 5, 2002
INVENTOR(S)  : Robert H. Shelton It is certified that error appears in the above-identified patent and that said Letters Patent is hereby corrected as shown below:

Column 1,
Line 38, "doctor" should read -- doctor's --.
Line 51, "loss" should read -- cost --.

Column 4,
Line 24, the line should read -- by the inventor hereof --.

Column 6,
Line 29, "design" should read -- diagram --.
Line 42, "principals" should read -- principles --.

Column 8,
Line 22, "appointment" should read -- appointments --.

Column 13,
Line 4, between "includes" and "for", insert -- means --.

Signed and Sealed this

Twenty-first Day of January, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,345,260 B1 Page 1 of 1
APPLICATION NO. : 09/039614
DATED : February 5, 2002
INVENTOR(S) : Robert H. Shelton It is certified that error appears in the above-identified patent and that said Letters Patent is hereby corrected as shown below:

On the title page, item (75) Inventors should read as follows:

--(75) Inventor: Robert H. Shelton, Irvine, CA (US)--.

Signed and Sealed this

Fourth Day of July, 2006

JON W. DUDAS
*Director of the United States Patent and Trademark Office*

UNITED STATES PATENT AND TRADEMARK OFFICE
CERTIFICATE OF CORRECTION

PATENT NO. : 6,345,260 B1 Page 1 of 1
APPLICATION NO. : 09/039614
DATED : February 5, 2002
INVENTOR(S) : Robert H. Shelton It is certified that error appears in the above-identified patent and that said Letters Patent is hereby corrected as shown below:

On the title page, item (75) Inventors should read as follows:
--(75) Inventor: Robert H. Shelton, Irvine CA (US)--.

Signed and Sealed this

Eighteenth Day of July, 2006

JON W. DUDAS
*Director of the United States Patent and Trademark Office*